United States Patent [19]

Warrellow et al.

[11] Patent Number: 5,891,896
[45] Date of Patent: Apr. 6, 1999

[54] TRI-SUBSTITUTED PHENYL DERIVATIVES USEFUL AS PDE IV INHIBITORS

[75] Inventors: Graham John Warrellow, Northwood; Julien Alistair Brown, Reading, both of United Kingdom

[73] Assignee: Celltech Therapeutics Ltd., Berkshire, United Kingdom

[21] Appl. No.: 769,466

[22] Filed: Dec. 20, 1996

[30] Foreign Application Priority Data

Dec. 21, 1995 [GB] United Kingdom .................... 9526243

[51] Int. Cl.$^6$ ........................ A61K 31/44; C07D 213/44; C07D 213/56; C07D 213/61
[52] U.S. Cl. .......................... 514/357; 514/277; 546/332; 546/334; 546/337; 546/339
[58] Field of Search .................... 546/332, 337, 546/339, 334; 514/357, 277

[56] References Cited

U.S. PATENT DOCUMENTS

| | | | |
|---|---|---|---|
| 4,012,495 | 3/1977 | Schmiechen et al. | 514/424 |
| 4,015,017 | 3/1977 | Gazave | 514/687 |
| 4,153,713 | 5/1979 | Huth et al. | 514/423 |
| 4,193,926 | 3/1980 | Schmiechen et al. | 548/517 |
| 4,303,649 | 12/1981 | Jones | 514/18 |
| 4,788,195 | 11/1988 | Torley et al. | 514/252 |
| 4,792,561 | 12/1988 | Walker et al. | 514/312 |
| 4,876,252 | 10/1989 | Torley et al. | 514/224.8 |
| 4,897,396 | 1/1990 | Hubele | 514/275 |
| 4,921,862 | 5/1990 | Walker et al. | 514/312 |
| 4,966,622 | 10/1990 | Rempfler et al. | 71/92 |
| 4,971,959 | 11/1990 | Hawkins | 514/150 |
| 5,124,455 | 6/1992 | Lombardo | 546/181 |
| 5,128,358 | 7/1992 | Saccomano et al. | 514/392 |
| 5,159,078 | 10/1992 | Rempfler et al. | 544/330 |
| 5,175,167 | 12/1992 | Zipperer et al. | 514/277 |
| 5,177,085 | 1/1993 | Naef | 514/307 |
| 5,236,918 | 8/1993 | Amschler et al. | 514/247 |
| 5,274,002 | 12/1993 | Hawkins | 514/530 |
| 5,298,511 | 3/1994 | Waterson | 514/311 |
| 5,326,898 | 7/1994 | Chandraratna | 560/17 |
| 5,340,827 | 8/1994 | Beeley et al. | 514/352 |
| 5,491,147 | 2/1996 | Boyd et al. | 514/247 |
| 5,521,184 | 5/1996 | Zimmermann | 514/252 |
| 5,550,137 | 8/1996 | Beeley et al. | 514/354 |
| 5,580,888 | 12/1996 | Warrellow et al. | 514/332 |
| 5,608,070 | 3/1997 | Alexander et al. | 546/274 |
| 5,693,659 | 12/1997 | Head et al. | 514/357 |
| 5,723,460 | 3/1998 | Warrellow et al. | 514/247 |
| 5,739,144 | 4/1998 | Warrellow et al. | 514/277 |

FOREIGN PATENT DOCUMENTS

| | | |
|---|---|---|
| 0 233 461 A2 | 8/1987 | European Pat. Off. . |
| 0 295 210 A1 | 12/1988 | European Pat. Off. . |
| 2 545 356 A1 | 11/1994 | France . |
| WO 95/35281 | 12/1995 | WIPO . |
| WO 95/35283 | 12/1995 | WIPO . |
| WO 97/09297 | 3/1997 | WIPO . |

OTHER PUBLICATIONS

Ashton, "Selective Type IV Phosphodiesterase Inhibitors as Antiasthmatic Agents. The Syntheses and Biological Activities of 3–(Cyclopentyloxy)–4–methyoxybenzamides and Analogues", *J. Med. Chem.*, 1994, 37, 1696–1703.

Beavo & Reifsnyder, "Primary Sequence of Cyclic Nucleotide Phosphodiesterase Isozymes and the Design of Selective Inhibitors" *TIPS*, 1990, 11, 150–155.

Buu–Hoi, N.P. et al., "Bromination of Some 1,2,2–Triarylethylenes" *J. of Organic Chemistry*, 1958, 1261–1263.

Buu–Hoi et al., "New Method for the Synthesis of ω,ω–Diarylacetophenones Aminated in the Aromatic Nucleus. Plynitration of Triarylethylenes", *Chem. Abstr.*, 1964, 61(13), 16006h.

Chan, A.C. et al., "The Role of Protein Tyrosine Kinases and Protein Tyrosine Phosphates in T Cel Antigen Receptor Signal Transduction", *Annu. Rev. Immunol.*, 1994, 12, 555–592.

Daves, G.D. et al., "Pyrimidines, XIII. 2– and 6–Substituted 4–Pyrimidinecarboxylic Acids", *J. of Hev. Chem.*, 1964, 1, 130–133.

Dietl, F. et al., "Chinone von Benzo–und Dibenzokronenethern", *Synthesis*, 1985, 626–631.

El–Wakil et al., "Study of the Proton magnetic resonance of methoxytamozifen towards ortho–substitution", *Chem. Abstr.*, 1992, 116, 255248t.

Geissler, J.F. et al., "Thiazolidine–Diones. Biochemical and Biological Activity of a Novel Class of Tyrosine Protein Kinase Inhibitors", *J. of Biol. Chem.*, 1990, 265(36), 22255–22261.

Hanks, S.K. et al., "The eukaryotic protein kinase superfamily: kinase (catalytic) domain structures and classification", *FASEB J.*, 1995, 9, 576–596.

Hirose et al., "Styrene Derivatives and Electrophotographic Photoreceptor Containing Them", *Chem. Abstr.*, 1993, 118, 136183z.

(List continued on next page.)

*Primary Examiner*—Alan L. Rotman
*Attorney, Agent, or Firm*—Woodcock Washburn Kurtz Mackiewicz & Norris LLP

[57] ABSTRACT

Tri-substituted phenyl derivatives and pharmaceutical compositions containing them. In a preferred embodiment, the compounds have the general formula (2):

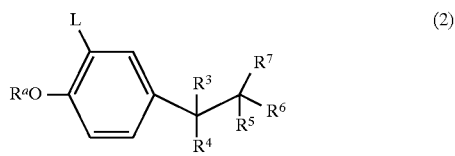

(2)

wherein L is preferably —OR$^1$; R$^a$ is preferably optionally substituted alkyl; R$^1$ is preferably optionally substituted indanyl; R$^3$ is preferably hydrogen, fluorine, hydroxy or an optionally substituted straight or branched chain alkyl group; R$^4$ and R$^5$ are preferably independently —(CH$_2$)$_t$Ar, where t is zero or an integer 1, 2 or 3 wherein Ar is preferably optionally substituted monocyclic or bicyclic aryl or optionally substituted monocyclic or bicyclic heteroaryl; and R$^6$ and R$^7$ are preferably independently hydrogen, fluorine or optionally substituted alkyl. Compounds of the invention are potent and selective phosphodiesterase type IV inhibitors and are useful in the prophylaxis and treatment of various diseases, such as asthma, which are associated with an unwanted inflammatory response or muscular spasm.

8 Claims, No Drawings

OTHER PUBLICATIONS

Ishikura, M. et al., "An Efficient Synthesis of 3–Heteroarylpyridines via Diethyl–(3–pyridyl)–borane" *Synthesis*, 1984, 936–938.

Iwashita, S. et al., "Signal Transduction System for Growth Factor Receptor Associated with Tyrosine Kinase Activity; Epidermal Growth Factor Receptor Singalling and Its Regulation", *Cellular Signalling*, 1992, 4(2), 123–132.

Lisle, H. et al., "IL–2–Induced Eosinophilia in the Rat Pleural Cavity: The Effect of Dexamethasone and Indomethacin", *Br. J. Pharmacol.* 1993, 108, 230.

Livi et al., "Cloning and Expression of cDNA for a Human Low–$K_m$3 Rolipram–sensitive Cyclic AMP Phosphodiesterase", *Molecular and Cellular Biol.* 1990, 10(6), 2678–2686.

Manhas et al., "heterocyclic Componds XII. Quinazoline Derivatives as Potential Antifertility Agents(1)" *J. Heterocyclic Chem.*, 1979, 16, 711–715.

Meyers, A.J. et al., "Oxazolines. XI. Synthesis of Functionalized Aromatic and Aliphaic Acids. A Useful Protecting Group for Carboxylic Acids Against Grignard and Hybrid Reagents", *J. Org. Chem.* 1974, 39(18), 2787–2793.

Mezheritskaya, "Synthesis and properties of carboxonium het=erocyclic systems. VIII. Synthesis and properties of 2–benzyl–substituted 1,3–dioxolanium salts", *Chem. Abstr.*, 1980, 93, 95160j, 635.

Mitsunobu, O., "The Use of Diethyl Azodicarboxylate and Triphenylphosphine in Synthesis and Transformation of Natural Products" *Synthesis*, 1981, 1–28.

Newton, A.C., "Protein Kinase C: Structure, Function, Regulation", *J. Biol. Chem.*, 1995, 270(48), 28495–28498.

Nicholson et al., "Differential Modulation of Tissue Function and Therapeutic Potential of Selective Inhibitors of Cyclic Nucleotide Phosphodiesterase Isoenzymes" *TIPS*, 1991, 12, 19–27.

O'Connor et al., "Voltammetry and Controlled Potential Oxidation of 3,4–dimethoxpropenylbenzene at a rotating electrode in unbuffered acetonitrile and in acetonitrile–pyridine solution" *Chem. Abstr.*, 1964, 60(8) #10203.4.

Ohtani, Y. et al., "Studies on Pitch Problems Caused by Pulping and Bleaching of Tropical Woods, XIV. Chemistry of the Aurone Derivatives at the Conventional Bleaching Stages", *Acta Chem. Scand.*, 1982, 613–621.

Pines, J., "Cycline and cyclin–dependent kinases: take your partners", *TIBS*, 1993, 18, 195–197.

Plé, N. et al., "Metalation of Diazines. XI. Directed Ortho–Lithiation of Fluoropyrimidines and Application to Synthesis of an Azacarboline", *J. Heterocyclic Chem.*, 1994, 31, 1311–1315.

Porter et al., "Preparation of 6–phenyl–3–(5–tetrazolyl)pyridin–=2(H)–one Derivatives as Cyclic AMP–dependent Protein Kinase Agonists" *Chem. Abstr.*, 1992, 117(9), 90296n.

Ramalingam, Deshmukh and Sattur, "Synthesis and Pharmacology of 2,5–Disubstituted 1,3,4–Zxadiazoles" *J. Indian Chem. Soc.*, 1981, 58(3), 269–271.

Reddy et al., "Inhibition of Breast Cancer Cell Growth in Vitro by a Tyrosine Kinase Inhibitor" *Cancer Research*, 1992, 52, 3636–3641.

Sáchez, H.I. et al., "Formal Total Synthesis of β–Pipitzol", *Tetrahedron*, 1985, 41(12), 2355–2359.

Schneider et al., "Catechol Estrogens of the 1,1,2–Triphenylbut–1–ene Type: Relationship Between Structure, Estradiol Receptor Affinity, Estrogenic and Antiestrogenic Properties, and Mammary Tumor Inhibiting Activities" *J. Med. Chem.*, 1986, 29, 1355–1362.

Seitz et al., "Fluorotamoxifen. A Caveat on the Generality of Electrophilic Destannylation" *Chem. Abstr.*, 1989, 111, 57133k.

Sharp, M.J. et al., "Synthetic Connections to the Aromatic Directed Metalation Reaction. Functionalized Aryl Boronic Acids by Ipso Borodesilylation; General Synthesis of Unsymmetrical iphenyls and n–Terphenyls", *Tetrahedron Lett.*, 1987, 28(43), 5093–5096.

Thompson, W.J. and Guadino, J., "A General Synthesis of 5–Arylnicotinates" *J. Org. Chem.*, 1994 49, 5237–5243.

Yeadon et al., "Mechanisms Contributing to Ozone–Induced Bronchial Hyperreactivity in Guinea Pigs", *Pulmonary Pharm.*, 1992, 5, 39–50.

Yoneda et al., "The Antiproliferative Effects of Tyrosine Kinase Inhibitors Tyrophostins on a Human Squamous Cell Carcinoma in Vitro and in Nude Mice" *Cancer Research*, 1991, 51, 4430–4435.

Sakakibara, K. et al., "Preparation of N–pyridyl–4–(benzyloxy) benzamides as Cardiotonics", *Chem. Abstr.*, 1988, 108, No. 131583p.

Tsutsumi, K. et al., "Preparation of (Dialkoxyphosphinoylmethyl)benzamides as Antihyperlipidemics", *Chem. Abstr.*, 1990, 113, No. 6599a.

Chatterjee, A. et al., "Total Synthesis of Ring–C Aromatic 18–Nor Steroid", *Tetrahedron*, 1980, 36, 2513–2519.

Clayton, S.E. et al., "Direct Aromatic tert–Butylation during the Synthesis of Thiochroman–4–ones", *Tetrahedron*, 1993, 49 (4), 939–946.

Collins, R.F. et al., "The Chemotherapy of Schistosomiasis. Part IV. Some Ethers of 4–Amino–2–methoxyphenol", *J. Chem. Soc.*, 1961, 1863–1879.

Degani, I. et al., "Cationi etero–aromatici Nota VI—Sintesi di alcuni derivati del perclorato di tiacromilio", *Boll. Sci. Fac. Chim. Ind. Bologna*, 1966, 24 (2–3), 75–91 (English Summary Only).

Geissler et al., "Biochemical and Biological Activity of a Novel Class of Tyrosine Protein Kinase Inhibitors", *J. Biol. Chem.*, 1990, 265 (36), 22255–22261.

Griffin, R.W. et al., "1–Methyl–7–halo–2–naphthalenecarboxylic Acid Derivatives", *J. Organic Chem.*, 1964, 29(8), 2109–2116.

Gupta, A.S. et al., "Friedel–Crafts Condensation of Ethyl Allylmalonate with Anisole", *Tetrahedron*, 1967, 23, 2481–2490.

Hart et al., "Alkylation of Phenol with a Homoallylic Halide", *J. Am. Chem. Soc.*, 1963, 85, 3269–3273.

Johnson et al., "Identification of Retinoic Acid Receptor β Subtype Specific Agonists", *J. Med. Chem.*, 1996, 39 (26), 5027–5030.

Lehmann, J. et al., "Lactones; XIII. Grignard Reaction Followed by Phase–Transfer Oxidation: A Convenient Synthesis of γ,γ–Distributed γ–Butyrolactones from γ–Butyrolactone", *Synthesis*, 1987, 1064–1067 (English abstract only).

Meyers, A.I. et al., "The Synthesis of 2–Pyridones from Cyclic Cyano Ketones. A New Aromatization Procedure for Dihydro–2–pyridones", *J. Org. Chem.*, 1964, 29, 1435–1438.

Kefalas, P. et al., "Signaling by the $p60^{c-src}$ Family of Protein–Tyrosine Kinases", *Int. J. Biochem. Cell Biol.*, 1995, 27(6), 551–563.

TRI-SUBSTITUTED PHENYL DERIVATIVES USEFUL AS PDE IV INHIBITORS

This invention relates to a novel series of triarylethanes, to processes for their preparation, to pharmaceutical compositions containing them, and to their use in medicine.

Many hormones and neurotransmitters modulate tissue function by elevating intra-cellular levels of adenosine 3', 5'-cyclic monophosphate (cAMP). The cellular levels of cAMP are regulated by mechanisms which control synthesis and breakdown. The synthesis of cAMP is controlled by adenyl cyclase which may be directly activated by agents such as forskolin or indirectly activated by the binding of specific agonists to cell surface receptors which are coupled to adenyl cyclase. The breakdown of cAMP is controlled by a family of phosphodiesterase (PDE) isoenzymes, which also control the breakdown of guanosine 3',5'-cyclic monophosphate (cGMP). To date, seven members of the family have been described (PDE I–VII) the distribution of which varies from tissue to tissue. This suggests that specific inhibitors of PDE isoenzymes could achieve differential elevation of cAMP in different tissues, [for reviews of PDE distribution, structure, function and regulation, see Beavo & Reifsnyder (1990) TIPS, 11: 150–155 and Nicholson et al (1991) TIPS, 12: 19–27].

There is clear evidence that elevation of cAMP in inflammatory leukocytes leads to inhibition of their activation. Furthermore, elevation of cAMP in airway smooth muscle has a spasmolytic effect. In these tissues, PDE IV plays a major role in the hydrolysis of cAMP. It can be expected, therefore, that selective inhibitors of PDE IV would have therapeutic effects in inflammatory diseases such as asthma, by achieving both anti-inflammatory and bronchodilator effects.

In our International Patent Specification No. WO94/14742 we describe a series of triarylethanes which are potent inhibitors of the PDE IV isoenzyme at concentrations at which they have little or no inhibitory action on other PDE isoenzymes. The compounds are of use in medicine, especially in the prophylaxis and treatment of asthma. An enantioselective process for the preparation of these compounds is described in our International Patent Specification No. WO95/17386.

We have now found a particular series of triarylethanes which are potent and selective PDE IV inhibitors and which also have other advantageous pharmacological properties, including especially improved metabolic stability.

Thus according to one aspect of the invention, we provide a compound of formula (1)

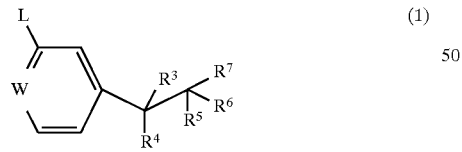

wherein

=W— is (1) =C(Y)— where Y is a halogen atom, or an alkyl or —XR$^a$ group where X is —O—, —S(O)$_p$— [where p is zero or an integer of value 1 or 2], or —N(R$^b$)— [where R$^b$ is a hydrogen atom or an optionally substituted alkyl group] and R$^a$ is a hydrogen atom or an optionally substituted alkyl group or, (2) =N—;

L is a —XR$^1$ group where R$^1$ is an optionally substituted fused ring bicyclic hydrocarbon optionally containing one or more heteroatoms or groups;

R$^3$ is a hydrogen or a fluorine atom, an optionally substituted straight or branched alkyl group, or a hydroxyl group;

R$^4$ is a hydrogen atom or group —(CH$_2$)$_t$Ar [where t is zero or an integer 1, 2 or 3 and Ar is a monocyclic or bicyclic aryl group, optionally containing one or more heteroatoms selected from oxygen, sulphur or nitrogen atoms] or a group —(CH$_2$)$_t$—Ar—(L$^1$)$_n$—Ar' [where L$^1$ is a divalent linking group n is zero or an integer 1, and Ar' is —Ar, —CO(Alk)$_m$Ar, [where Alk is an optionally substituted straight or branched C$_{1-6}$ alkylene, C$_{2-6}$ alkenylene or C$_{2-6}$ alkynylene chain optionally interrupted by one, two or three —O— or —S— atoms or —S(O)q— (where q is an integer 1 or 2) or —N(R$^b$)— groups and m is zero or an integer 1], —SO$_2$(Alk)$_m$Ar, —SO$_2$NH(Alk)$_m$Ar, —SO$_2$N(Alk$^1$)(Alk)$_m$Ar [where Alk$^1$ is as defined for Alk] —SO$_2$N[(Alk)$_m$Ar]$_2$, —CONH(Alk)$_m$Ar, —CON(Alk$^1$)(Alk)$_m$Ar, —CON[(Alk)$_m$Ar]$_2$, —N(Alk$^1$)SO$_2$(Alk)$_m$Ar, —NHSO$_2$(Alk)$_m$Ar, —N[SO$_2$(Alk)$_m$Ar]$_2$, —NHSO$_2$NH(Alk)$_m$Ar, —N(Alk$^1$)SO$_2$NH(Alk)$_m$Ar, —NHSO$_2$N(Alk$^1$)(Alk)$_m$Ar, —N(Alk$^1$)SO$_2$N(Alk$^1$)(Alk)$_m$Ar, —NHSO$_2$N[(Alk)$_m$Ar]$_2$, —N(Alk$^1$)SO$_2$N[(Alk)$_m$Ar]$_2$, —NHC(O)(Alk)$_m$Ar, —N(Alk$^1$)C(O)(Alk)$_m$Ar, —N[C(O)(Alk)$_m$Ar]$_2$, —NHC(O)NH(L$^2$)$_r$(Alk)$_m$Ar, [where L$^2$ is a divalent linker group and r is zero or an integer 1], —N(Alk$^1$)C(O)NH(L$^2$)$_r$(Alk)$_m$Ar, —NHC(O)N(Alk$^1$)(L$^2$)$_r$(Alk)$_m$Ar, —N(Alk$^1$)C(O)N(Alk$^1$)(L$^2$)$_r$(Alk)$_m$Ar, —NHC(O)O(Alk)$_m$Ar, —N(Alk$^1$)C(O)O(Alk)$_m$Ar, —C(S)NH(Alk)$_m$Ar, —C(S)N(Alk$^1$)(Alk)$_m$Ar, —C(S)N(Alk$^1$)(Alk)$_m$Ar, —C(S)N[(Alk)$_m$Ar]$_2$, —NHC(S)(Alk)$_m$Ar, —N(Alk$^1$)C(S)(Alk)$_m$Ar, —N[C(S)(Alk)$_m$Ar]$_2$, —NHC(S)NH(L$^2$)$_r$(Alk)$_m$Ar, —N(Alk$^1$)C(S)NH(L$^2$)$_r$(Alk)$_m$Ar, —NHC(S)N(Alk$^1$)(L$^2$)$_r$(Alk)$_m$Ar, —N(Alk$^1$)C(S)N(Alk$^1$)(L$^2$)$_r$(Alk)$_m$Ar, —SO$_2$(Alk)$_m$NHet [where —NHet is an optionally substituted C$_{5-7}$ heterocyclic amino group optionally containing one or more other —O— or —S— atoms or —N(R$^b$)—, —C(O)— or —C(S)— groups], —CO(Alk)$_m$NHet, —CS(Alk)$_m$NHet, —NHSO$_2$(Alk)$_m$NHet, —NHC(O)(Alk)$_m$NHet, —NHC(S)(Alk)$_m$NHet, —SO$_2$NH[(Alk)$_m$Het'] [where Het' is an optionally substituted C$_{5-7}$monocyclic carbocyclic group optionally containing one or more —O— or —S— atoms or —N(R$^b$)— groups], —CONH[(Alk)$_m$Het'], —CSNH[(Alk)$_m$Het'], —NHSO$_2$NH[(Alk)$_m$Het'], —NHC(O)NH(Alk)$_m$(Het') or —NHC(S)NH(Alk)$_m$(Het')];

R$^5$ is a —(CH$_2$)$_t$Ar or —(CH$_2$)$_t$—Ar—(L$^1$)$_n$—Ar' group;

R$^6$ is a hydrogen or a fluorine atom, or an optionally substituted alkyl group;

R$^7$ is a hydrogen or a fluorine atom, an optionally substituted straight or branched alkyl group or an OR$^c$ group where R$^c$ is a hydrogen atom or an optionally substituted alkyl or alkenyl group, or an alkoxyalkyl, alkanoyl, formyl, carboxamido or thiocarboxamido group; and the salts, solvates, hydrates, prodrugs and N-oxides thereof.

It will be appreciated that certain compounds of formula (1) may have one or more chiral centres, depending on the nature of the groups R$^1$, R$^3$, R$^4$, R$^5$, R$^6$ and R$^7$. Where one or more chiral centres is present, enantiomers or diastereomers may exist, and the invention is to be understood to extend to all such enantiomers, diastereomers and mixtures thereof, including racemates.

In the compounds of formula (1), when =W— is =C(Y)— and Y is a halogen atom Y may be for example a fluorine, chlorine, bromine or iodine atom.

When W in the compounds of formula (1) is a group =C(Y)— and Y is —XR$^a$, R$^a$ may be, for example, a hydrogen atom or an optionally substituted straight or branched alkyl group, for example, an optionally substituted $C_{1-6}$alkyl group, such as a methyl, ethyl, n-propyl or i-propyl group. Optional substituents which may be present on $R^a$ groups include one or more halogen atoms, e.g. fluorine, or chlorine atoms. Particular $R^a$ groups include for example —$CH_2F$, —$CH_2Cl$, —$CHF_2$, —$CHCl_2$, —$CF_3$ or —$CCl_3$ groups.

When =W— in the compounds of formula (1) is a group =C(Y)— where —Y is —N($R^b$), =W— may be a =C($NH_2$)—, =C($NHCH_3$)— or =C($NHC_2H_5$)— group.

In compounds of formula (1), X may be an oxygen or a sulphur atom, or a group —S(O)—, —S(O)$_2$—, —NH— or $C_{1-6}$ alkylamino, for example a $C_{1-3}$ alkylamino, e.g. methylamino [—N($CH_3$)—] or ethylamino [—N($C_2H_5$)—] group.

Alkyl groups represented by Y, R, $R^1$, $R^2$, or $R^b$ in the compounds of formula (1) include optionally substituted straight or branched $C_{1-6}$ alkyl groups optionally interrupted by one or more X atoms or groups. Particular examples include $C_{1-3}$ alkyl groups such as methyl or ethyl groups. Optional substituents on these groups include one, two or three substituents selected from halogen atoms, e.g. fluorine, chlorine, bromine or iodine atoms, or hydroxyl or $C_{1-6}$alkoxy e.g. $C_{1-3}$alkoxy such as methoxy or ethoxy or —$CO_2R^8$ [where $R^8$ is a hydrogen atom or an optionally substituted alkyl, aralkyl or aryl group], —$CONR^9R^{10}$ [where $R^9$ and $R^{10}$, which may be the same or different is each as defined for $R^8$], —$CSNR^9R^{10}$ or —CN groups. Particular $CO_2R^8$, —$CONR^9R^{10}$ or $CSNR^9R^{10}$ substituents include for example —$CO_2H$, —$CONH_2$ or —$CSNH_2$ groups or a group —$CO_2R^8$, —$CONR^9R^{10}$, —$CSNR^9R^{10}$, —$CONHR^{10}$, —$CSNHR^{10}$ where $R^8$, $R^9$ and $R^{10}$ where present is a $C_{1-3}$alkyl group such as methyl or ethyl group, a $C_{6-12}$aryl group, for example an optionally substituted phenyl, or a 1- or 2-naphthyl group, or a $C_{6-12}$aryl $C_{1-3}$alkyl group such as an optionally substituted benzyl or phenethyl group. Optional substituents which may be present on these aryl groups include $R^{13}$ substituents discussed below in relation to the group Ar.

The fused ring bicyclic hydrocarbon represented by $R^1$ in compounds of formula (1) may be an optionally substituted fused ring bicyclic $C_{7-10}$ hydrocarbon optionally containing one or more, e.g. two, heteroatoms or groups selected from for example oxygen, sulphur or nitrogen atoms or —N($R^b$)— groups.

The fused ring bicyclic hydrocarbon will in general have one ring of aromatic character and the other of alicyclic character. Particular examples include indanyl and 1, 2, 3, 4-tetrahydronaphthalene groups, each optionally containing one or two oxygen, sulphur or nitrogen atoms or —N($R^b$)— groups in the aromatic and/or alicyclic rings, such as indoline and isoindoline groups. In general, the hydrocarbon will be attached to the remainder of the molecule of formula (1) through any available ring carbon atom.

Optional substituents which may be present on $R^1$ hydrocarbon groups include, for the aromatic ring portion, those $R^{13}$ substituents discussed below in relation to the groups Ar and Ar', and, for the alicyclic ring portion, one or two halogen atoms or $C_{1-3}$alkyl, e.g. methyl, $C_{1-3}$alkoxy, e.g. methoxy or hydroxyl groups.

When the group $R^7$ in compounds of formula (1) is an $OR^c$ group it may be for example a hydroxyl group, or a group —$OR^c$ where $R^c$ is an optionally substituted straight or branched $C_{1-6}$alkyl group, e.g. a $C_{1-3}$alkyl group such as a methyl or ethyl group, a $C_{2-6}$alkenyl group such as an ethenyl or 2-propen-1-yl group, a $C_{1-3}$alkoxy$C_{1-3}$alkyl group such as a methoxymethyl, ethoxymethyl or ethoxyethyl group, a $C_{1-6}$alkanoyl, e.g. $C_{1-3}$alkanoyl group such as an acetyl group, or a formyl [HC(O)—], carboxamido ($CONR^{12}R^{12a}$) or thiocarboxamido ($CSNR^{12}R^{12a}$) group, where $R^{12}$ and $R^{12a}$ in each instance may be the same or different and is each a hydrogen atom or an optionally substituted straight or branched $C_{1-6}$alkyl, e.g. $C_{1-3}$alkyl group such as methyl or ethyl group. Optional substituents which may be present on such $R^c$, $R^{12}$ or $R^{12a}$ groups include those described below in relation to the alkyl groups $R^6$ or $R^7$.

Alkyl groups represented by $R^3$, $R^6$ or $R^7$ in compounds of formula (1) include optionally substituted straight or branched $C_{1-6}$ alkyl groups, e.g. $C_{1-3}$ alkyl groups such as methyl, ethyl, n-propyl or i-propyl groups. Optional substituents which may be present on these groups include one or more halogen atoms, e.g. fluorine, chlorine, bromine or iodine atoms, or hydroxyl or $C_{1-6}$alkoxy e.g. $C_{1-3}$alkoxy such as methoxy or ethoxy groups.

When the group $R^6$ in compounds of formula (1) is a halogen atom it may be for example a fluorine, chlorine, bromine or iodine atom.

In the compounds of formula (1), the groups —$(CH_2)_rAr$ and —$(CH_2)_rAr(L^1)_nAr'$ when present may be —Ar, —$CH_2Ar$, —$(CH_2)_2Ar$, —$(CH_2)_3Ar$—, —Ar—Ar', —Ar-$L^1$—Ar', —$CH_2ArAr'$, —$CH_2ArL^1Ar'$, —$(CH_2)_2ArAr'$, —$(CH_2)_2ArL^1Ar'$, —$(CH_2)_3ArAr'$ or —$(CH_2)_3ArL^1Ar'$ groups.

Monocyclic or bicyclic aryl groups represented by the group Ar or Ar' in compounds of formula (1) include for example $C_{6-12}$ optionally substituted aryl groups, for example optionally substituted phenyl, 1-or 2-naphthyl, indenyl or isoindenyl groups.

When the monocyclic or bicyclic aryl group Ar or Ar' contains one or more heteroatoms, Ar or Ar' may be for example a $C_{1-9}$ optionally substituted heteroaryl group containing for example one, two, three or four heteroatoms selected from oxygen, sulphur or nitrogen atoms. In general, Ar or Ar' heteroaryl groups may be for example monocyclic or bicyclic heteroaryl groups. Monocyclic heteroaryl groups include for example five- or six-membered heteroaryl groups containing one, two, three or four heteroatoms selected from oxygen, sulphur or nitrogen atoms. Bicyclic heteroaryl groups include for example nine- or ten-membered heteroaryl groups containing one, two or more heteroatoms selected from oxygen, sulphur or nitrogen atoms.

Examples of heteroaryl groups represented by Ar or Ar' include pyrrolyl, furyl, thienyl, imidazolyl, N-methylimidazolyl, N-ethylimidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, pyridyl, pyrimidinyl, pyridazinyl, pyrazinyl, 1,3,5-triazinyl, 1,2,4-triazinyl, 1,2,3-triazinyl, benzofuryl, isobenzofuryl, benzothienyl, isobenzothienyl, indolyl, isoindolyl, benzimidazolyl, benzothiazolyl, benzoxazolyl, quinazolinyl, naphthyridinyl, pyrido[3,4-b]pyridyl, pyrido[3,2-b]pyridyl, pyrido[4,3-b] pyridyl, quinolinyl, isoquinolinyl, tetrazolyl, 5,6,7,8-tetrahydroquinolinyl and 5,6,7,8-tetrahydroisoquinolinyl. Example of bicyclic heteroaryl groups include quinolinyl or isoquinolinyl groups.

The heteroaryl group represented by Ar or Ar' may be attached to the remainder of the molecule of formula (1) through any ring carbon or heteroatom as appropriate. Thus, for example, when the group Ar or Ar' is a pyridyl group it may be a 2-pyridyl, 3-pyridyl or 4-pyridyl group. When it is a thienyl group it may be a 2-thienyl or 3-thienyl group, and, similarly, when it is a furyl group it may be a 2-furyl or 3-furyl group. In another example, when the group Ar or Ar' is a quinolinyl group it may be a 2-, 3-, 4-, 5-, 6-, 7- or 8-quinolinyl and when it is an isoquinolinyl, it may be a 1-, 3-, 4-, 5-, 6-, 7- or 8-isoquinolinyl group.

When in compounds of formula (1) the Ar or Ar' group is a nitrogen-containing heterocycle it may be possible to form quaternary salts, for example N-alkyl quaternary salts and the invention is to be understood to extend to such salts. Thus for example when the group Ar or Ar' is a pyridyl group, pyridinium salts may be formed, for example N-alkylpyridinium salts such as N-methylpyridinium.

The aryl or heteroaryl groups represented by Ar or Ar' in compounds of formula (1) may each optionally be substituted by one, two, three or more substituents [$R^{13}$]. The substituent $R^{13}$ may be selected from an atom or group $R^{14}$ or —$Alk^2(R^{14})_m$ wherein $R^{14}$ is a halogen atom, or an amino (—$NH_2$), substituted amino, nitro, cyano, hydroxyl (—OH), substituted hydroxyl, cycloalkoxy, formyl [HC(O)—], carboxyl (—$CO_2H$), esterified carboxyl, thiol (—SH), substituted thiol, —C(O)$Alk^2$, —$SO_3H$, —$SO_2Alk^2$, —$SO_2NH_2$, —$SO_2NHAlk^2$, —$SO_2N[Alk^2]_2$, —$CONH_2$, —$CONHAlk^2$, $CON[Alk^2]_2$, —$NHSO_2H$, —$NAlk^2SO_2H$, —$NHSO_2Alk^2$, —$NAlk^2SO_2Alk^2$, —$N[SO_2Alk^2]_2$, —$NHSO_2NH_2$, —$NAlk^2SO_2NH_2$, —$NHSO_2NHAlk^2$, —$NAlk^2SO_2NHAlk^2$, —$NHSO_2N[Alk^2]_2$, —$NAlk^2SO_2N[Alk^2]_2$, —NHC(O)H, —NHC(O)$Alk^2$, —$NAlk^2C(O)H$, —$NAlk^2C(O)Alk^2$, —$N[C(O)Alk^2]_2$, —NHC(O)OH, —NHC(O)O$Alk^2$, —$NAlk^2C(O)OH$, —$NAlk^2C(O)OAlk^2$, —$NHCONH_2$, —$NHCONHAlk^2$, —$NHCON[Alk^2]_2$, —$NAlk^2CON[Alk^2]_2$, —$NAlk^2CONH[Alk^2]$, —$NAlk^2CONH_2$, —C(S)H, —C(S)$Alk^2$, —$CSNH_2$, —$CSNHAlk^2$, —$CSN[Alk^2]_2$, —NHC(S)H, —$NHCSAlk^2$, —$NAlk^2C(S)H$, —$NAlk^2C(S)Alk^2$, —$N[C(S)Alk^2]_2$, —$N[C(O)Alk^2]SO_2H$, —$NHCSNH_2$, —$NHCSNHAlk^2$, —$NHCSN[Alk^2]_2$, —$NAlk^2CSN[Alk^2]_2$, —$NAlk^2CSNHAlk^2$, —$NAlk^2CSNH_2$, or —$N[C(O)Alk^2]SO_2Alk^2$ group, $Alk^2$ is a straight or branched $C_{1-6}$ alkylene, $C_{2-6}$alkenylene, or $C_{2-6}$alkynylene chain optionally interrupted by one, two, or three —O—, or —S— atoms or —S(O)p—, [where p is an integer 1 or 2] or —N($R^8$)— groups; and m is zero or an integer 1, 2 or 3.

When in the group —$Alk^2(R^{14})_m$ m is an integer 1, 2 or 3, it is to be understood that the substituent or substituents $R^{14}$ may be present on any suitable carbon atom in —$Alk^2$. Where more than one $R^{14}$ substituent is present these may be the same or different and may be present on the same or different carbon atom in $Alk^2$. Clearly, when m is zero and no substituent $R^{14}$ is present or when $Alk^2$ forms part of a group such as —$SO_2Alk^2$ the alkylene, alkenylene or alkynylene chain represented by $Alk^2$ becomes an alkyl, alkenyl or alkynyl group.

When $R^{14}$ is a substituted amino group it may be a group —NH[$Alk^2(R^{14a})_m$] [where $Alk^2$ and m are as defined above and $R^{14a}$ is as defined above for $R^{14}$ but is not a substituted amino, a substituted hydroxyl or a substituted thiol group] or a group —N[$Alk^2(R^{14a})_m]_2$ wherein each —$Alk^2(R^{14a})_m$ group is the same or different.

When $R^{14}$ is a halogen atom it may be for example a fluorine, chlorine, bromine, or iodine atom.

When $R^{14}$ is a cycloalkoxy group it may be for example a $C_{5-7}$cycloalkoxy group such as a cyclopentyloxy or cyclohexyloxy group.

When $R^{14}$ is a substituted hydroxyl or substituted thiol group it may be a group —O$Alk^2(R^{14a})_m$ or —S$Alk^2(R^{14a})_m$ respectively, where $Alk^2$, $R^{14a}$ and m are as just defined.

Esterified carboxyl groups represented by the group $R^{14}$ include groups of formula —$CO_2Alk^3$ wherein $Alk^3$ is a straight or branched, optionally substituted $C_{1-8}$alkyl group such as a methyl, ethyl, n-propyl, i-propyl, n-butyl, i-butyl, s-butyl or t-butyl group; a $C_{6-12}$aryl$C_{1-8}$alkyl group such as an optionally substituted benzyl, phenylethyl, phenylpropyl, 1-naphthylmethyl or 2-naphthylmethyl group; a $C_{6-12}$aryl group such as an optionally substituted phenyl, 1-naphthyl or 2-naphthyl group; a $C_{6-12}$aryloxy$C_{1-8}$alkyl group such as an optionally substituted phenyloxymethyl, phenyloxyethyl, 1-naphthyloxymethyl, or 2-naphthyloxymethyl group; an optionally substituted $C_{1-8}$alkanoyloxy$C_{1-8}$alkyl group, such as a pivaloyloxymethyl, propionyloxyethyl or propionyloxypropyl group; or a $C_{6-12}$aroyloxy$C_{1-8}$alkyl group such as an optionally substituted benzoyloxyethyl or benzoyloxypropyl group. Optional substituents present on the $Alk^3$ group include $R^{13}$ substituents described above.

It will be appreciated that the group Ar or Ar' may be attached to the remainder of the molecule of formula (1) through either a ring carbon atom or heteroatom.

Particular examples of the chain $Alk^2$ when present include methylene, ethylene, n-propylene, i-propylene, n-butylene, i-butylene, s-butylene, t-butylene, ethenylene, 2-propenylene, 2-butenylene, 3-butenylene, ethynylene, 2-propynylene, 2-butynylene or 3-butynylene chain, optionally interrupted by one, two, or three —O— or —S—, atoms or —S(O)—, —S(O)$_2$— or —N($R^b$)— groups.

Particularly useful atoms or groups represented by $R^{13}$ include fluorine, chlorine, bromine or iodine atoms, or $C_{1-6}$alkyl, e.g. methyl or ethyl, $C_{1-6}$alkylamino, e.g. methylamino or ethylamino, $C_{1-6}$ hydroxyalkyl, e.g. hydroxymethyl or hydroxyethyl, $C_{1-6}$alkylthiol e.g. methylthiol or ethylthiol, $C_{1-6}$alkoxy, e.g. methoxy or ethoxy, $C_{5-7}$cycloalkoxy, e.g. cyclopentyloxy, halo$C_{1-6}$alkyl, e.g. trifluoromethyl, $C_{1-6}$alkylamino, e.g. methylamino or ethylamino, amino (—$NH_2$), amino$C_{1-6}$alkyl, e.g. aminomethyl or aminoethyl, $C_{1-6}$dialkylamino, e.g. dimethylamino or diethylamino, nitro, cyano, hydroxyl (—OH), formyl [HC(O)—], carboxyl (—$CO_2H$), —$CO_2Alk^3$ [where $Alk^3$ is as defined above], $C_{1-6}$ alkanoyl e.g. acetyl, thiol (—SH), thio$C_{1-6}$alkyl, e.g. thiomethyl or thioethyl, sulphonyl (—$SO_3H$), $C_{1-6}$alkylsulphonyl, e.g. methylsulphonyl, aminosulphonyl (—$SO_2NH_2$), $C_{1-6}$alkylaminosulphonyl, e.g. methylaminosulphonyl or ethylaminosulphonyl, $C_{1-6}$dialkylaminosulphonyl, e.g. dimethylaminosulphonyl or diethylaminosulphonyl, carboxamido (—$CONH_2$), $C_{1-6}$alkylaminocarbonyl, e.g. methylaminocarbonyl or ethylaminocarbonyl, $C_{1-6}$dialkylaminocarbonyl, e.g. dimethylaminocarbonyl or diethylaminocarbonyl, sulphonylamino (—$NHSO_2H$), $C_{1-6}$alkylsulphonylamino, e.g. methylsulphonylamino or ethylsulphonylamino, $C_{1-6}$dialkylsulphonylamino, e.g. dimethylsulphonylamino or diethylsulphonylamino, aminosulphonylamino (—$NHSO_2NH_2$), $C_{1-6}$alkylaminosulphonylamino, e.g. methylaminosulphonylamino or ethylaminosulphonylamino, $C_{1-6}$dialkylaminosulphonylamino, e.g. dimethylaminosulphonylamino or diethylaminosulphonylamino, $C_{1-6}$alkanoylamino, e.g. acetylamino, $C_{1-6}$alkanoylamino$C_{1-6}$alkyl, e.g. acetylaminomethyl or $C_{1-6}$ alkoxycarbonylamino, e.g. methoxycarbonylamino, ethoxycarbonylamino or t-butoxycarbonylamino thiocarboxamido (—$CSNH_2$), $C_{1-6}$ alkylaminothiocarbonyl, e.g. methylaminothiocarbonyl or ethylaminothiocarbonyl, $C_{1-6}$dialkylaminothiocarbonyl, e.g. dimethylaminothiocarbonyl or diethylaminothiocarbonyl, aminocarbonylamino, $C_{1-6}$alkylaminocarbonylamino, e.g. methylaminocarbonylamino or ethylaminocarbonylamino, $C_{1-6}$dialkylaminocarbonylamino, e.g. dimethylaminocarbonylamino or diethylaminocarbonylamino, aminothiocarbonylamino, $C_{1-6}$alkylaminothiocarbonylamino, e.g. methylaminothiocarbonylamino or ethylaminothiocarbonylamino, $C_{1-6}$ dialkylaminothiocarbonylamino, e.g. dimethylaminothiocarbonylamino, or diethylaminothiocarbonylamino, aminocarbonylsamino$C_{1-6}$ alkyamino, e.g. aminocarbonylmethylamino or aminocarbonylethylamino, aminothiocarbonyl$C_{1-6}$ alkylamino e.g. aminothiocarbonylmethylamino or aminothiocarbonylethylamino, formylamino$C_{1-6}$ alkylsulphonylamino, e.g. formylaminomethylsulphonylamino or formyl-aminoethylsulphonylamino, thioformylamino$C_{1-6}$alkylsulphonylamino, e.g. thioformylaminomethylsulphonylamino or thioformylethylsulphonylamino, $C_{1-6}$acylaminosulphonylamino, e.g. acetylaminosulphonylamino, $C_{1-6}$thioacylaminosulphonylamino, e.g. thioacetylaminosulphonylamino groups.

Where desired, two $R^{13}$ substituents may be linked together to form a cyclic group such as a cyclic ether, e.g. a $C_{2-6}$alkylenedioxy group such as ethylenedioxy.

It will be appreciated that where two or more $R^{13}$ substituents are present, these need not necessarily be the same atoms and/or groups. The $R^{13}$ substituents may be present at any ring carbon atom away from that attached to the rest of the molecule of formula (1). Thus, for example, in phenyl groups represented by Ar or Ar' any substituent may be present at the 2-, 3-, 4-, 5- or 6- positions relative to the ring carbon atom attached to the remainder of the molecule.

In the compounds of formula (1), when the group —$(CH_2)_rAr(L^1)_nAr'$ is present in $R^4$ and/or $R^5$, the linker group $L^1$ may be any divalent linking group. Particular examples of $L^1$ groups which may be present in compounds of the invention include groups of formula —$(Alk^4)_r(X^a)_s(Alk^5)_t$— where $Alk^4$ and $Alk^5$ is each an optionally substituted straight or branched $C_{1-6}$alkylene, $C_{2-6}$alkenylene or $C_{2-6}$alkynylene chain optionally interrupted by one or more, e.g. one, two or three heteroatoms or carbocyclic or heteroatom-containing groups, $X^a$ is an —O— or —S— atom or a —S(O)—, —S(O)$_2$— or —N(R$^b$)— group, r is zero or the integer 1, t is zero or the integer 1 and s is zero or the integer 1, provided that when one of r, s, or t is zero at least one of the remainder is the integer 1.

The heteroatoms which may interrupt the $Alk^4$ or $Alk^5$ chains include for example —O— or —S— atoms. Carbocyclic groups include for example cycloalkyl, e.g. cyclopentyl or cyclohexyl, or cycloalkenyl e.g. cyclopentenyl or cyclohexenyl, groups. Particular heteroatom-containing groups which may interrupt $Alk^4$ or $Alk^5$ include oxygen-, sulphur- or nitrogen-containing groups such as —S(O)—, —S(O)$_2$—, —N(R$^b$)—, —C(O)—, —C(S)—, —C(NR$^b$)—, —CON(R$^b$)—, —CSN(R$^b$)—, —N(R$^b$)CO—, —N(R$^b$)CS—, —SON(R$^b$)—, —SO$_2$N(R$^b$)—, —N(R$^b$)SO—, —N(R$^b$)SO$_2$—, —N(R$^b$)SO$_2$N(R$^b$)—, —N(R$^b$)SON(R$^b$)—, or —N(R$^b$)CON(R$^b$)— groups. It will be appreciated that when the chains $Alk^4$ or $Alk^5$ are interrupted by two or more heteroatoms, carbocyclic or heteroatom-containing groups, such atoms or groups may be adjacent to one another, for example to form a group —N(R$^b$)—C(NR$^b$)—N(R$^b$)— or —O— CONH—.

Optional substituents which may be present on $Alk^4$ or $Alk^5$ chains include those described above in relation to the group $R^1$ when it is an alkyl group.

The group —$(L^1)_nAr'$ may be attached to the group Ar through any available carbon or heteroatoms present in the two groups. Thus, for example, when Ar is a phenyl group, —$(L^1)_nAr'$ may be attached through a carbon or heteroatom in —$(L^1)_nAr'$ to a carbon atom in Ar at the 2-, 3-, 4-, 5-, or 6-position relative to the Ar carbon atom attached to the remainder of the molecule.

In the group $(L^1)_nAr'$ particular examples of $Alk^4$ or $Alk^5$ include optionally substituted methylene, ethylene, propylene, butylene, ethenylene, 2-propenylene, 2-butenylene, 3-butenylene, ethynylene, 2-propynylene, 2-butynylene or 3-butynylene chains, optionally interrupted by one, two or three heteroatoms, carbocyclic or heteroatom-containing groups as described above.

Particular examples of the group —$(L^1)_nAr'$ include the groups —$Alk^4Ar'$, —$XAr'$, —$Alk^4XAr'$ and —$XAlk^5Ar'$, especially for example —$CH_2Ar'$, —$(CH_2)_2Ar'$, —$(CH_2)_3Ar'$, —$CH_2OCH_2Ar'$, —$CH_2SCH_2Ar'$, —$CH_2N(R^b)CH_2Ar'$, —CH=CHAr', —$CH_2CH$=CHAr', —OAr', —SAr', —N(R$^b$)Ar', —$CH_2OAr'$, —$CH_2SAr'$, —$CH_2N(R^b)Ar'$, —$CH_2OCH_2OAr'$, —OCH$_2$Ar', —O(CH$_2$)$_2$Ar', —SCH$_2$Ar', —S(CH$_2$)$_2$Ar', —N(R$^b$)CH$_2$Ar' and —N(R$^b$)(CH$_2$)$_2$Ar'. In these particular groups, Ar' may be as generally described herein and as particularly described below.

In general, and in the particular groups just mentioned, Alk in Ar' may be an optionally substituted methylene, ethylene, n-propylene, i-propylene, n-butylene, s-butylene, t-butylene, ethenylene, 2-propenylene, 2-butenylene, 3-butenylene, ethynylene, 2-propenylene, 2-butynylene, or 3-butynylene chain optionally interrupted by one, two or three —O— or —S— atoms or —S(O)—, —S(O)$_2$— or —N(R$^b$)— groups. Optional substituents which may be present include one or more halogen atoms, e.g. fluorine, chlorine, bromine or iodine atoms, or hydroxyl or $C_{1-6}$alkoxy e.g. $C_{1-3}$alkoxy such as methoxy or ethoxy groups. The group $Alk^1$ when present in Ar' may also be as just described for Alk, but will clearly be an alkyl, alkenyl or alkynyl group, rather than a corresponding alkylene, alkenylene or alkynylene chain.

The divalent linking group $L^2$ when present in Ar' groups may be for example a —S(O), —S(O)N(R$^b$)—, —S(O)$_2$—, —S(O)$_2$N(R$^b$)—, —C(O)—, —C(O)N(R$^b$)—, —C(S)— or —C(S)N(R$^b$)— group.

Particular examples of the group Ar' include optionally substituted $C_{6-12}$aryl or $C_{1-9}$heteroaryl groups, especially optionally substituted phenyl or pyridyl groups, or, Ar$^1$ may be in particular, —CO(Alk)$_m$Ph (where Ph is an optionally substituted phenyl group), —SO$_2$(Alk)$_m$Ar, —SONH(Alk)$_m$Ph, —SO$_2$N(Alk$^1$)(Alk)$_m$Ph, —SO$_2$N[(Alk)$_m$Ph]$_2$, —CONH(Alk)$_m$Ph, —CON(Alk$^1$)(Alk)$_m$Ph, —CON[(Alk)$_m$Ph]$_2$, —NAlk$^1$SO$_2$(Alk)$_m$Ph, —NHSO$_2$N(Alk$^1$)(Alk)$_m$Ph, —NAlk$^1$SO$_2$Alk$^1$(Alk)$_m$Ph, —NHSO$_2$N[(Alk)$_m$Ph]$_2$, —NAlk$^1$SO$_2$N[(Alk)$_m$Ph]$_2$, —NHC(O)(Alk)$_m$Ph, —NAlk$^1$CO(Alk)$_m$Ph, —NHC(O)N[(Alk)$_m$Ph]$_2$, —NHC(O)NH(L$^2$)$_r$(Alk)$_m$Ph, —NAlk$^1$C(O)NH(L$^2$)$_r$(Alk)$_m$Ph, —NHC(O)N(Alk$^1$)(L$^2$)$_r$(Alk)$_m$Ph, —NAlk$^1$C(O)N(Alk$^1$)(L$^2$)$_r$(Alk)$_m$Ph, —NHC(O)O(Alk)$_m$Ph, —NAlk$^1$C(O)O(Alk)$_m$Ph, —C(S)NH(Alk)$_m$Ph, —C(S)N(Alk$^1$)(Alk)$_m$Ph, —N(S)N[(Alk)$_m$Ph]$_2$, —NHC(S)(Alk)$_m$Ph, —N(Alk$^1$)C(S)(Alk)$_m$Ph, —N[C(S)(Alk)$_m$Ph]$_2$, —NHC(S)NH(L$^2$)$_r$(Alk)$_m$Ph, —NAlk$^1$C(S)NH(L$^2$)$_r$(Alk)$_m$Ph, —NHC(S)N(Alk$^1$)(L$^2$)$_r$(Alk)$_m$Ph, or —N(Alk$^1$)C(S)N(Alk$^1$)((L$^2$)$_r$Alk)$_m$Ph groups. In these groups, the groups Alk and $Alk^1$ may in particular each be a methylene or ethylene, and a methyl or ethyl group respectively and m may be zero or in particular 1, and r may be zero or 1.

When in $R^4$ and/or $R^5$ a —NHet group is present this may be for example a pyrrolidinyl, pyrazolidinyl, piperidinyl, morpholinyl, piperazinyl or thiomorpholinyl group.

Optional substituents that may be present in such groups include $R^{13}$ substituents described above in relation to Ar or Ar' groups.

When in $R^4$ and/or $R^5$ a Het' group is present this may be for example a pyrrolidinyl, pyrazolidinyl, piperidinyl, morpholinyl, piperazinyl, thiomorpholinyl, cyclopentyl, or cyclohexyl group. Optional substituents that may be present on such groups include $R^{13}$ substituents described above.

In the compounds of formula (1), when an ester group is present, for example a group $CO_2R^8$ or —$CO_2Alk^3$ this may advantageously be a metabolically labile ester.

The presence of certain substituents in the compounds of formula (1) may enable salts of the compounds to be formed. Suitable salts include pharmaceutically acceptable salts, for example acid addition salts derived from inorganic or organic acids, and salts derived from inorganic and organic bases.

Acid addition salts include hydrochlorides, hydrobromides, hydroiodides, alkylsulphonates, e.g. methanesulphonates, ethanesulphonates, or isethionates, arylsulphonates, e.g. p-toluenesulphonates, besylates or napsylates, phosphates, sulphates, hydrogen sulphates, acetates, trifluoroacetates, propionates, citrates, maleates, fumarates, malonates, succinates, lactates, oxalates, tartrates and benzoates.

Salts derived from inorganic or organic bases include alkali metal salts such as sodium or potassium salts, alkaline earth metal salts such as magnesium or calcium salts, and organic amine salts such as morpholine, piperidine, dimethylamine or diethylamine salts.

Prodrugs of compounds of formula (1) include those compounds, for example esters, alcohols or aminos, which are convertible in vivo by metabolic means, e.g. by hydrolysis, reduction, oxidation or transesterification, to compounds of formula (1).

Particularly useful salts of compounds according to the invention include pharmaceutically acceptable salts, especially acid addition pharmaceutically acceptable salts.

In the compounds of formula (1) the group =W— is preferably a =C(Y)— group. In compounds of this type Y is preferably a —$XR^a$ group where X is —O— and $R^a$ is an optionally substituted ethyl group or, especially, an optionally substituted methyl group. Especially useful substituents which may be present on $R^a$ groups include one, two or three fluorine or chlorine atoms.

One particularly useful group of compounds of the invention has the formula (1) wherein L is a group —$OR^1$.

The groups $R^4$ and $R^5$ in compounds of formula (1) is each, independently, preferably a —$(CH_2)_r$Ar or —$(CH_2)_r$Ar—$(L^1)_n$—Ar' group, particularly a $CH_2$Ar or —$CH_2$Ar$(L^1)_n$Ar' group or especially an —Ar, Ar-Ar' or Ar$L^1$Ar' group. Particularly useful $R^4$ or $R^5$ groups of this type include those groups in which Ar or Ar' is a monocyclic aryl group optionally containing one or more heteroatoms selected from oxygen, sulphur, or, in particular, nitrogen atoms, and optionally substituted by one, two, three or more $R^{13}$ substituents. In these compounds, when the group represented by Ar or Ar' is a heteroaryl group it is preferably a nitrogen-containing monocyclic heteroaryl group, especially a six-membered nitrogen-containing heteroaryl group. Thus, in one preferred example, the groups $R^4$ and $R^5$ may each contain a six-membered nitrogen-containing heteroaryl Ar or Ar' group. In another preferred example $R^4$ may contain a monocyclic aryl group or a monocyclic or bicyclic heteroaryl group Ar or Ar' containing one or more oxygen, sulphur or nitrogen atoms and $R^5$ may contain a six-membered nitrogen-containing heteroaryl group Ar or Ar'. In these examples, the six-membered nitrogen-containing heteroaryl group may be an optionally substituted pyridyl, pyridazinyl, pyrimidinyl, pyrazinyl or imidazolyl group. Particular examples include optionally substituted 2-pyridyl, 3-pyridyl, 5-imidazolyl, or, especially, 4-pyridyl, 3-pyridazinyl, 4-pyridazinyl, 5-pyridazinyl, 2-pyrimidinyl, 4-pyrimidinyl, 5-pyrimidinyl, 2-pyrazinyl or 3-pyrazinyl. The monocyclic aryl group may be a phenyl group or a substituted phenyl group, and the monocyclic or bicyclic heteroaryl group containing one or more oxygen, sulphur or nitrogen atom may be an optionally substituted 2-furyl, 3-furyl, 2-thienyl, 3-thienyl, 2-thiazolyl, 2-benzo(b) thiophenyl, 2-benzo(b)furyl or 4-isoquinolinyl group.

In another preference relating to $R^4$ groups of the just mentioned particular types, Ar' is a —NHC(O)NH(Alk)$_m$Ph (where Ph is as previously described above) —NHCH$_3$C(O)NH(Alk)$_m$Ph, —NHC(O)N(CH$_3$)(Alk)$_m$Ph, —N(CH$_3$)C(O)N(CH$_3$)(Alk)$_m$Ph, —NHCONHSO$_2$Ph, —CO(Alk)$_m$Ph, —NHSO$_2$NH(Alk)$_m$Ph, —N(CH$_3$)SO$_2$NH(Alk)$_m$Ph, —N(CH$_3$)SO$_2$N(CH$_3$)(Alk)$_m$Ph, —NHCO(Alk)$_m$Ph, —N(CH$_3$)CO(Alk)$_m$Ph or —NHSO$_2$(Alk)$_m$Ph group.

In general in compounds of formula (1) when $R^4$ and/or $R^5$ contains a substituted phenyl group it may be for example a mono-, di- or trisubstituted phenyl group in which the substituent is an atom or group $R^{13}$ as defined above. When the $R^4$ and/or $R^5$ group contains a monosubstituted phenyl group the substituent may be in the 2-, or preferably 3-, or especially 4-position relative to the ring carbon atom attached to the remainder of the molecule. When the $R^4$ and/or $R^5$ group contains a disubstituted phenyl group, the substituents may be in the 2,6 position relative to the ring carbon atom attached to the remainder of the molecule.

Particularly useful substituents $R^{13}$ which may be present on Ar groups in $R^4$ and $R^5$, especially on phenyl groups, include halogen atoms or alkyl, haloalkyl, amino, substituted amino, nitro, —NHSO$_2$NH$_2$, —NHSO$_2$NHCH$_3$, —NHSO$_2$N(CH$_3$)$_2$, —NHCOCH$_3$, —NHC(O)NH$_2$, —NCH$_3$C(O)NH$_2$, —NHC(O)NHCH$_3$, —NHC(O)NHCH$_2$CH$_3$, or —NHC(O)N(CH$_3$)$_2$ groups, each of said atoms or groups being optinally separated from the remainder of the Ar group by a group Alk$^2$ as defined above.

When in compounds of formula (1) $R^4$ and/or $R^5$ contains a substituted pyridyl group it may be for example a mono- or disubstituted pyridyl group, such as a mono- or disubstituted 2-pyridyl, 3-pyridyl or especially 4-pyridyl group substituted by one or two atoms or groups $R^{13}$ as defined above, in particular one or two halogen atoms such as fluorine or chlorine atoms, or methyl, methoxy, hydroxyl or nitro groups. Particularly useful pyridyl groups of these types are 3-monosubstituted-4-pyridyl or 3,5-disubstituted-4-pyridyl, or 2- or 4-monosubstituted-3-pyridyl or 2,4-disubstituted-3-pyridyl groups.

A particularly useful group of compounds of formula (1) has the formula (2):

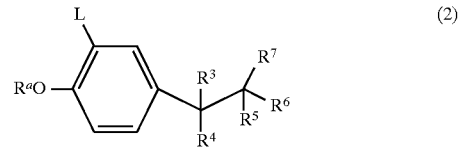

where —L is a OR$^1$ group and R$^1$ is an optionally substituted indanyl group R$^a$ is an optionally substituted alkyl group and R$^3$, R$^4$, R$^5$, R$^6$ and R$^7$ are as defined for formula (1); and the salts, solvates, hydrates, prodrugs and N-oxides thereof.

In compounds of formula (2) and in general in compounds of formula (1) any indanyl group represented by R$^1$ may be a 1-indanyl or 2-indanyl group.

In the compounds of formulae (1) or (2) one preferred group of compounds are those where the group $R^3$ is a hydrogen atom; the group $R^6$ is a methyl group, or especially a hydrogen atom; the group $R^7$ is a methyl group, or especially a hydrogen atom; and $R^4$ and $R^5$ are as defined for formula (1). In compounds of this type $R^6$ and $R^7$ is each especially a hydrogen atom.

In general in compounds of formulae (1) or (2) $R^3$, $R^6$ and $R^7$ is each especially a hydrogen atom, $R^5$ is in particular a —$(CH_2)_t$ Ar group, especially an optionally substituted pyridyl group, especially a 4-pyridyl group and $R^4$ is in particular a Ar or —Ar—$(L^1)_n$—Ar' group. Particular examples of such —Ar—$(L^1)_n$—Ar' groups include —Ar—NHC(O)NH(Alk)$_m$Ar, —Ar—CH$_2$NHC(O)NH(Alk)$_m$Ar, —Ar—CO(Alk)$_m$Ar, —Ar—CH$_2$CO(Alk)$_m$Ar, —Ar—NHSO$_2$NH(Alk)$_m$Ar, —Ar—CH$_2$NHSO$_2$NH(Alk)$_m$Ar, —Ar—NHSO$_2$(Alk)$_m$Ar, —Ar—CH$_2$NHSO$_2$(Alk)$_m$Ar, —Ar—NCH$_3$C(O)NH(Alk)$_m$Ar, —Ar—CH$_2$NCH$_3$C(O)NH(Alk)$_m$Ar, —Ar—NCH$_3$SO$_2$NH(Alk)$_m$Ar or —Ar—CH$_2$NCH$_3$SO$_2$NH(Alk)$_m$Ar groups. In these $R^4$ groups Ar may in particular be an optionally substituted phenyl group. Optional substituents include for example, halogen atoms, e.g. chlorine or fluorine atoms, alkyl, e.g. methyl, haloalkyl, e.g. trifluoromethyl, amino, substituted amino, e.g. methylamino, ethylamino, dimethylamino, nitro, —NHSO$_2$NH$_2$, —NHSO$_2$NHCH$_3$, —NHSO$_2$N(CH$_3$)$_2$, —NHCOCH$_3$, —NHC(O)NH$_2$, —NCH$_3$C(O)NH$_2$, —NHC(O)NHCH$_3$, —NHC(O)NHCH$_2$CH$_3$, or —NHC(O)N(CH$_3$)$_2$ groups, each of said atoms or groups being optionally separated from the remainder of the phenyl group by a —CH$_2$— group. The group Alk in the above examples may be as described generally for compounds of formula (1) and may in particular be an optionally substituted $C_{1-6}$alkylene chain such as a methylene or ethylene chain.

In the above examples, when Ar is a phenyl group, the —$(L^1)_n$Ar group or any other optional substituent may be attached to any available ring carbon atom away from that attached to the remainder of the compound of formula (1). In particular the group —$(L^1)_n$Ar' may be attached at the 4-position, or especially the 3-position of the phenyl ring.

Particularly useful compounds according to the invention are:

(R)-4-[1-(3-(2-Indanyloxy)-4-methoxyphenyl)-2-(4-pyridyl)ethyl]aniline;

(R)-4-{2-(3-(2-Indanyloxy)-4-methoxyphenyl)-2-[4-(benzylsulphonylamino)phenyl]ethyl}pyridine;

(R)-N-[4-{1-(3-(2-Indanyloxy)-4-methoxyphenyl)-2-(4-pyridyl)ethyl}-phenyl]-N'-ethylurea;

and the salts, solvates, hydrates, prodrugs and N-oxides thereof.

Compounds according to the invention are selective and potent inhibitors of PDE IV and advantageously have improved metabolic stability. The ability of the compounds to act in this way may be simply determined by the tests described in the Examples hereinafter.

Particular uses to which the compounds of the invention may be put include the prophylaxis and treatment of asthma, especially inflamed lung associated with asthma, cystic fibrosis, or in the treatment of inflammatory airway disease, chronic bronchitis, eosinophilic granuloma, psoriasis and other benign and malignant proliferative skin diseases, endotoxic shock, septic shock, ulcerative colitis, Crohn's disease, reperfusion injury of the myocardium and brain, inflammatory arthritis, chronic glomerulonephritis, atopic dermatitis, urticaria, adult respiratory distress syndrome, diabetes insipidus, allergic rhinitis, allergic conjunctivitis, vernal conjunctivitis, arterial restenosis and artherosclerosis.

Compounds of the invention may also suppress neurogenic inflammation through elevation of cAMP in sensory neurones. They are, therefore, analgesic, anti-tussive and anti-hyperalgesic in inflammatory diseases associated with irritation and pain.

Compounds according to the invention may also elevate cAMP in lymphocytes and thereby suppress unwanted lymphocyte activation in immune-based diseases such as rheumatoid arthritis, ankylosing spondylitis, transplant rejection and graft versus host disease.

Compounds according to the invention may also reduce gastric acid secretion and therefore can be used to treat conditions associated with hypersecretion.

Compounds of the invention may suppress cytokine synthesis by inflammatory cells in response to immune or infectious stimulation. They are, therefore, useful in the treatment of bacterial, fungal or viral induced sepsis and septic shock in which cytokines such as tumour necrosis factor (TNF) are key mediators. Also compounds of the invention may suppress inflammation and pyrexia due to cytokines and are, therefore, useful in the treatment of inflammation and cytokine-mediated chronic tissue degeneration which occurs in diseases such as rheumatoid or osteoarthritis.

Over-production of cytokines such as TNF in bacterial, fungal or viral infections or in diseases such as cancer, leads to cachexia and muscle wasting. Compounds of the invention may ameliorate these symptoms with a consequent enhancement of quality of life.

Compounds of the invention may also elevate cAMP in certain areas of the brain and thereby counteract depression and memory impairment.

Compounds of the invention may suppress cell proliferation in certain tumour cells and can be used, therefore, to prevent tumour growth and invasion of normal tissues.

For the prophylaxis or treatment of disease the compounds according to the invention may be administered as pharmaceutical compositions, and according to a further aspect of the invention we provide a pharmaceutical composition which comprises a compound of formula (1) together with one or more pharmaceutically acceptable carriers, excipients or diluents.

Pharmaceutical compositions according to the invention may take a form suitable for oral, buccal, parenteral, nasal, topical or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles and preservatives. The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds of formulae (1) and (2) may be formulated for parenteral administration by injection e.g. by bolus injection or infusion. Formulations for injection may be presented in unit dosage form, e.g. in glass ampoule or multi dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formulae (1) and (2) may also be formulated as a depot preparation. Such long acting formulations may be administered by implantation or by intramuscular injection.

For nasal administration or administration by inhalation, the compounds for use according to the present invention are conveniently delivered in the form of an aerosol spray presentation for pressurised packs or a nebuliser, with the use of suitable propellant, e.g. dichlorodifluoromethane, trichlorofluoromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

The quantity of a compound of the invention required for the prophylaxis or treatment of a particular inflammatory condition will vary depending on the compound chosen, and the condition of the patient to be treated. In general, however, daily dosages may range from around 100 ng/kg to 100 mg/kg e.g. around 0.01 mg/kg to 40 mg/kg body weight for oral or buccal administration, from around 10 ng/kg to 50 mg/kg body weight for parenteral administration and around 0.05 mg to around 1000 mg e.g. around 0.5 mg to around 1000 mg for nasal administration or administrating by inhalation or insufflation.

The compounds according to the invention may be prepared by the following processes. In the reactions described below it may be necessary to protect reactive functional groups, for example hydroxy, amino, thio, or carboxy groups, where these are desired in the final product, to avoid their unwanted participation in the reactions. Conventional protecting groups may be used in accordance with standard practice [see, for example, Green, T. W. in "Protective Groups in Organic Synthesis" John Wiley and Sons, 1981].

Thus according to a further aspect of the invention a compound of formula (1) may be prepared by reaction of an intermediate of formula (3)

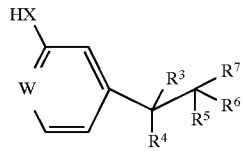
(3)

where W, X, $R^3$, $R^4$, $R^5$, $R^6$, and $R^7$ are as defined for formula (1), with a reagent $R^1L^3$ where $L^3$ is a leaving group.

Leaving groups represented by $L^3$ include halogen atoms such as bromine, chlorine or iodine atoms, or sulphonyloxy groups such as arylsulphonyloxy, e.g. p-toluenesulphonyloxy groups.

Depending on the exact nature of the starting material of formula (3), the reaction may be carried out using standard conditions for reactions of this type, for example where necessary in the presence of a base, e.g. an inorganic base such as a carbonate, e.g. caesium or potassium carbonate, an alkoxide, e.g. potassium-t-butoxide, or a hydride, e.g. sodium hydride, in a dipolar aprotic solvent such as an amide, e.g. a substituted amide such as dimethylformamide or an ether, e.g. a cyclic ether such as tetrahydrofuran, at ambient temperature or above, e.g. around 40° C. to 50° C.

In a variation of this general process, particularly where X in the starting material of formula (3) is an oxygen atom, the compound of formula (3) may be reacted with an alcohol $R^1OH$, in the presence of a phosphine, such as triphenylphosphine, and an activator, for example diethylazodicarboxylate, optionally in the presence of an organic base such as triethylamine, in a solvent such as tetrahydrofuran at ambient temperature up to the reflux temperature.

The intermediate starting materials of formula (1) may be prepared by any of the processes described in International Patent Specification Nos. WO94/14742, WO95/17386 or WO95/35281 or from any appropriate compound described therein using conventional procedures. Thus, for example, a compound of formula (3) may be prepared by treatment of a corresponding compound of formula (4)

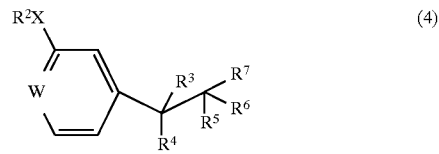
(4)

where $R^2$ is an alkyl or cycloalkyl, e.g. cyclopentyl, group and W, X, $R^3$, $R^4$, $R^5$, $R^6$ and $R^7$ are as previously defined, with an acid, e.g. concentrated sulphuric acid in a solvent such as an ether, e.g. a cyclic ether such as 1,4-dioxane at an elevated temperature e.g. the reflux temperature.

Reagents $R^1L^2$ or $R^1OH$ for use in the above processes are either known compounds or may be prepared using analogous methods to those used for the preparation of the known compounds.

Compounds of formula (1) may also be prepared by interconversion from other compounds of formula (1).

Thus according to a further aspect of the invention compounds of formula (1) may be prepared in a general substitution process by reaction of compound of formula (1) wherein at least one of $R^4$ or $R^5$ is a group $—(CH_2)_rArE^1$ (where $E^1$ is a leaving group or is, or contains, a reactive functional group) and a compound $AlkE^2$, $Ar'(L^1)_nE^2$ where $E^2$ is a hydrogen atom, or a group $E^1$ as just defined.

Particular examples of leaving groups represented by $E^1$ in these compounds include halogen atoms, e.g. a bromine atom, sulphonyloxy groups, e.g. an alkyl- or arylsulphonyloxy group, a boronic acid $[—B(OH)_2]$ or a tin reagent, e.g. $—Sn(CH_3)_3$. Particular reactive functional groups represented by or contained in $E^1$ include for example amines, particularly primary or secondary amines, $—CO_2H$ and reactive derivatives thereof, $—OH$, $—SO_3H$ and reactive derivatives thereof, carboxamides, e.g. $—CONH_2$, thiocarboxamides, e.g. $—CSNH_2$, ureas, e.g. $—NHCONH_2$, thioureas, e.g. $—NHCSNH_2$, isocyanates and isothiocyanates.

Compounds of formulae $AlkE^2$ or $Ar'(L^1)_nE^2$ are either known compounds or may be prepared from known starting materials using analogous processes to the known compounds. In these compounds, the group $E^2$ is either a hydrogen atom or a group E¹, including for example the particular E¹ groups just described.

The reaction conditions employed in this substitution process will depend on the precise nature of the reactants and the reaction desired but in general will involve standard approaches for reactions of these types.

Thus for example, where the substitution reaction is an acylation or thioacylation (for example where one of E¹ or E² is an amine and the other is an acyl halide or anhydride or a thioester) the acylation reaction may generally be performed in the presence of a base, such as a tertiary amine, e.g. triethylamine in a solvent such as a halogenated hydrocarbon e.g. dichloromethane at for example ambient temperature, and the thioacylation may for example be performed in an inert solvent such as tetrahydrofuran at a low temperature such as around 0° C.

Where the substitution reaction is a sulphonylation (for example where one of E¹ or E² is an amine and the other —(CH₂)ᵣArE¹, AlkE² or Ar'(L¹)ₙE² group contains for example a —SO₂Cl or equivalent reactive sulphonyl group) the reaction may be carried out optionally in the present of a base, for example an inorganic base such as sodium hydride in a solvent such as an amide, e.g. a substituted amide such as dimethylformamide or a halogenated hydrocarbon such as dichloromethane at for example ambient temperature.

In the instance where the substitution process is a coupling reaction (for example where E¹ is a leaving group such as a boronoic acid or a tin reagent and E² is a hydrogen atom) the reaction may be carried out in the presence of a complex metal catalyst, for example a heavy metal catalyst such as a palladium, e.g. tetrakis(triphenylphosphine) palladium, catalyst in an inert solvent, for example an aromatic hydrocarbon such as toluene or benzene, or an ether, such as dimethoxyethane or dioxane, if necessary in the presence of a base, e.g. an alkali carbonate such as sodium carbonate, at an elevated temperature, e.g. the reflux temperature. In general, the metal catalyst and reaction conditions may be selected, depending on the nature of the starting materials from a range of known alternatives for reactions of this type [see for example Miyaura, N et al, Synth. Comm. (1981), 11, 513; Thompson, W J and Gaudino, J., J. Org. Chem. (1984), 49, 5237; and Sharp M J et al, Tetrahedron Lett. (1987), 28, 5093].

In one particular example of a substitution reaction according to the invention, a compound of formula (1) wherein R⁴ and/or R⁵ contains a urea or thiourea group may be prepared by reaction of a corresponding intermediate compound of formula (1) wherein R⁴ and/or R⁵ contains an amino (—NH₂) group with an isocyanate AlkN=C=O or Ar(Alk)ₘ(L¹)ₙN=C=O or isothiocyanate AlkN=C=S or Ar(Alk)ₘ(L¹)ₙN=C=S. The reaction may be performed in a solvent, for example an organic solvent such as a halogenated hydrocarbon, e.g. dichloromethane where necessary in the presenece of a catalyst, e.g. dimethylaminopyridine, at around ambient temperature.

In a variation of this process the starting intermediate amine of formula (1) may first be treated with phosgene in the presence of a base, e.g. an organic amine such as triethylamine, and subsequently reacted with an amine Ar(Alk)ₘ(L¹)ₙNH₂ to yield the desired compound of formula (1) wherein R⁴ and/or R⁵ contains a urea group. The reaction may be carried out in an organic solvent such as a halogenated hydrocarbon, e.g dichloromethane, at from around 0° C. to ambient temperature.

N-oxides of compounds of formula (1) may be prepared for example by oxidation of the corresponding nitrogen base using an oxidising agent such as hydrogen peroxide in the presence of an acid such as acetic acid, at an elevated temperature, for example around 70° C. to 80° C., or alternatively by reaction with a peracid such as peracetic acid in a solvent, e.g. dichloromethane, at ambient temperature.

Salts of compounds of formula (1) may be prepared by reaction of a compound of formula (1) with an appropriate acid or base in a suitable solvent or mixture of solvents e.g. an organic solvent such as an ether e.g. diethylether, or an alcohol, e.g. ethanol using conventional procedures.

Where it is desired to obtain a particular enantiomer of a compound of formula (1) this may be produced from a corresponding mixture of enantiomers using any suitable conventional procedure for resolving enantiomers.

Thus for example diastereomeric derivatives, e.g. salts, may be produced by reaction of a mixture of enantiomers of formula (1) e.g. a racemate, and an appropriate chiral compound, e.g. a chiral acid or base. Suitable chiral acids include, for example, tartaric acid and other tartrates such as dibenzoyl tartrates and ditoluoyl tartrates, sulphonates such as camphor sulphonates, mandelic acid and other mandelates and phosphates such as 1,1'-binaphthalene-2,2'-diyl hydrogen phosphate. The diastereomers may then be separated by any convenient means, for example by crystallisation and the desired enantiomer recovered, e.g. by treatment with an acid or base in the instance where the diastereomer is a salt.

In another resolution process a racemate of formula (1) may be separated using chiral High Performance Liquid Chromatography.

Alternatively, a particular enantiomer may be obtained by using an appropriate chiral intermediate in one of the processes described above. Chiral intermediates may be obtained in particular by use of the enantioselective process described in International Patent Specification No. WO95/17386.

The following Examples illustrate the invention. The following abbreviations are used: THF—tetrahydrofuran; DEAD—diethylazodicarboxylate; DMAP—4-dimethylaminopyridine; RT—room temperature; PPh₃—triphenylphosphine.

The preparation of the following compounds is described:

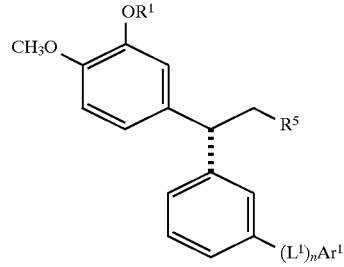

where R¹ is 2-indanyl, R⁵ is 4-pyridyl and (L¹)ₙAr' is:

Example 1: —NH₂

Example 2:

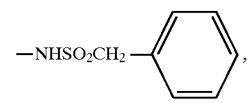

hydrochloride salt.

Example 3: —NHCONHCH₂CH₃, hydrochloride salt.

Intermediate 1

Water (25 ml) and sulphuric acid (40 ml, concentrated) was added to a solution of 3-[1-(R)-(3-cyclopentyloxy-4-methoxyphenyl)-2-(4-pyridyl)ethyl]aniline (3.8 g, 9.8 mmol prepared as described in International Patent specification No. WO95/17386) in 1,4-dioxane (50 ml) at RT. The mixture was heated at 90° C. for 1 h, cooled and concentrated in vacuo. The pH of the residue was adjusted to pH 8.0–8.5 by the addition of solid NaOH. The mixture was diluted with ethyl acetate (100 ml) and water (50 ml) and extracted with ethyl acetate (2×50 ml). The extract was washed with water (100 ml), brine (100 ml), dried ($MgSO_4$), filtered and concentrated in vacuo to give a crude product which was washed with ethyl acetate to afford 3-[1-(R)-(3-hydroxy-4-methoxyphenyl)-2-(4-pyridyl)ethyl]aniline (Intermediate 1) as a pale yellow powder (2.84 g, 91%). (Found: C, 73.83; H, 6.44; N, 8.09. $C_{20}H_{20}N_2O_2$+0.25 mol. eqv. of ethyl acetate requires C, 73.66; H, 6.48; N, 8.18%), $\delta_H$ ($d_4$-methanol) 3.3 (2H, d, J 8.0 Hz), 3.77 (3H, s), 4.06 (1H, t, J 8.0 Hz), 6.5 (1H, d, J 2.2 Hz), 6.53–6.78 (5H, m), 6.97 (1H, t, J 7.7 Hz), 7.13 (2H, d, J 5.8 Hz), and 8.25 (2H, d, J 5.6 Hz). m/z ($ESI\_MH^+$ 321 (25), 228 (100).

EXAMPLE 1

(R)-4-[1-(3-(2-Indanyloxy)-4-methoxyphenyl)-2-(4-pyridyl)ethyl]aniline

To a solution of Intermediate 1 (1.0 g, 3.1 mmol) in THF (25 ml) at RT was added $PPh_3$ (820 mg, 1 eq), 2-indanol (419 mg, 1 eq) and the solution stirred for 10 min prior to the addition of DEAD (492 μl, 1 eq). The reaction mixture was stirred at this temperature for 65 h before the further addition of 2-indanol (419 mg), $PPh_3$ (820 mg) and DEAD (492 μl). The mixture was stirred for an additional 1.5 h then quenched by the addition of water (10 ml). The mixture was diluted with ethyl acetate (100 ml), washed with water (4×50 ml), brine (50 ml), dried ($MgSO_4$), filtered and concentrated in vacuo to give a brown foam. The crude product was redissolved in ethyl acetate (50 ml) and extracted into hydrochloric acid (2×50 ml, 10% aq). The aqueous extract was basified (NaOH to pH>10) then extracted with ethyl acetate (2×100 ml). The extract was washed with water (2×50 ml), brine (50 ml), dried ($MgSO_4$), filtered and concentrated in vacuo to give a white foam. This was subjected to column chromatography ($SiO_2$; ethylacetate) to afford the title compound (856 mg, 63%) as a white foam. $\delta_H$ ($CDCl_3$) 3.05–3.35 (6H, m), 3.77 (3H, s), 4.06 (1H, t, J 8.0 Hz), 5.08 (1H, m), 6.52 (2H, d, J 7.8 Hz), 6.63 (1H, d, J 7.6 Hz), 6.70 (1H, s), 6.76 (2H, s), 6.95 (2H, d, J 6.0 Hz), 7.07 (1H, t, J 7.7 Hz), 7.18 (4H, m), and 8.41 (2H, d, J 5.9 Hz). m/z (ESI) 437 ($MH^+$, 100%), 459 ($MNa^+$, 2).

EXAMPLE 2

(R)-4-{2-(3-(2-Indanyloxy)-4-methoxyphenyl)-2-[4-(benzylsulphonylamino)phenyl]ethyl}pyridine hydrochloride Benzenesulphonyl chloride (50 μL) was added to a solution of the compound of Example 1 (0.141 g) in dichloromethane (2 ml) under $N_2$ at RT and stirred for 1.5 h. Diethylether (10 ml) was added and the resulting white precipitate filtered, washed with ether and dried in vacuo to afford the title compound (44 mg, 22%). (Found: C, 67.82, H, 5.42, N, 4.48. $C_{35}H_{32}N_2O_4S$. HCl ⅓$H_2O$ requires C, 67.89, H, 5.48, N, 4.52%); $\delta_8H$ ($CD_3OD$) 3.15–3.28 (2H, m), 3.4–3.55 (3H, m), 3.86 (2H, d, J 8.1 Hz), 3.92 (3H, s), 4.57–4.60 (1H, m), 5.32 (1H, m), 7.0–7.1 (3H, m), 7.21–8.1 (15H, m), and 8.83 (2H, d, J 6.65 Hz).

EXAMPLE 3

(R)-N-[4-{1-(3-(2-Indanyloxy)-4-methoxyphenyl)-2-(4-pyridyl)ethyl}phenyl]-N'-ethylurea hydrochloride To a solution of the aniline of Example 1 (50 mg, 1.15 mmol) in dichloromethane (5 ml) at RT was added DMAP (cat.) and ethyl isocyanate (100 μl, 1.1 eq) and the mixture stirred at this temperature overnight. The reaction mixture was concentrated in vacuo to yield a yellow foam, which was subjected to column chromatography ($SiO_2$; ethyl acetate) to afford the free base of the title compound (445 mg, 77%) as a white foam. The material was converted to its hydrochloride salt (Found: C, 68.89, H, 6.38; N, 7.81. $C_{32}H_{33}N_3O_3$. HCl. 0.75 $H_2O$ requires C, 68.93; H, 6.42; N, 7.54%). $\delta_H$ ($d_4$MeOH) 1.12 (3H, m), 2.96–3.30 (8H, m), 3.71 (3H, s), 4.36 (1H, t, J 8.0 Hz), 5.13 (1H, m), 6.87 (4H, m), 7.02 (1H, d, J 7.5 Hz), 7.11–7.16 (5H, m), 7.52 (1H, s), 7.83 (2H, br), and 8.58 (2H, br). m/z ESI 508 ($MH^+$, 100%), 530 ($MNa^+$, 3).

The advantageous pharmacological properties of the compounds according to the invention may be demonstrated in the following in vitro and ex vivo tests:

1. Isolated Recombinant Human PDE IVA Enzyme

A gene encoding human PDE IV has been cloned from human monocytes (Livi, et al., 1990, *Molecular and Cellular Biology*, 10, 2678). Using similar procedures we have cloned human PDE IV genes from a number of sources including eosinophils, neutrophils, lymphocytes, monocytes, brain and neuronal tissues. These genes have been transfected into yeast using an inducible vector and various recombinant proteins have been expressed which have the biochemical characteristics of PDE IV (*Beavo and Reifsnyder*, 1990, TIPS, 11, 150). These recombinant enzymes, particularly the human eosinophil recombinant PDE IVA, have been used as the basis of a screen for potent, selective PDE IV inhibitors.

The enzymes were purified to isoenzyme homogeneity using standard chromatographic techniques.

Phosphodiesterase activity was assayed as follows. The reaction was conducted in 150 μl of standard mixture containing (final concentrations): 50 mM 2-[[tris(hydroxymethyl)methyl]amino]-1-ethanesulphonic acid (TES) —NaOH buffer (pH 7.5), 10 mM $MgCl_2$, 0.1 μM [$^3$H]-cAMP and vehicle or various concentrations of the test compounds. The reaction was initiated by addition of enzyme and conducted at 30° C. for between 5 to 30 min. The reaction was terminated by addition of 50 μl 2% trifluoroacetic acid containing [$^{14}$C]-5'AMP for determining recovery of the product. An aliquot of the sample was then applied to a column of neutral alumina and the [$^3$H]-cAMP eluted with 10 ml 0.1 TES—NaOH buffer (pH8). The [$^3$H]-5'-AMP product was eluted with 2 ml 2M NaOH into a scintillation vial containing 10 ml of scintillation cocktail. Recovery of [$^3$H]-5'AMP was determined using the [$^{14}$C]-5'AMP and all assays were conducted in the linear range of the reaction. Results were expressed as $IC_{50}$ values.

Using this procedure, the compounds of Examples 2 and 3 for example had $IC_{50}$ values of 2.0 nM (compound of Example 2) and 34 nM (compound of Example 3).

The compounds of the Examples had little or no activity against other isolated PDE isoenzymes (specifically PDE I, II, III or V—see WO 94/14742 for experimental details) at concentrations up to 100 μM, thus illustrating the selectivity of their action against PDE IV.

2. Rat Hepatocyte Metabolism

The improved metabolic stability of the compounds according to the invention was demonstrated in a conventional rat hepatocyte model in which rat hepatocytes were cultured in the presence of test compound. The quantity of compound remaining after a fixed period of time was then determined using mass spectroscopy.

In this test, for example, the compounds of Examples 2 and 3 remain substantially unmetabolised after 3 h with 80% and over of each compound remaining at the end of this period. This compares favourably with related compounds, for example compounds in which $R^4$ and/or $R^5$ is —$(CH_2)_t$—Ar and Ar is phenyl as described in WO94/14742 which are extensively metabolised in 3 h.

We claim:

1. A compound of formula (3)

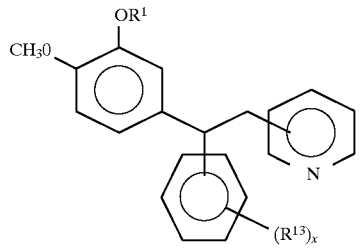

(3)

wherein:

x is 0 or an integer 1, 2 or 3;

$R^1$ is an indanyl group; and $R^{13}$ is an alkyl, —$NH_2$, —$NHAlk^2$, —$N(Alk^2)_2$, —$NHSO_2NH_2$, —$NHSO_2NHAlk^2$, —$NHSO_2N(Alk^2)_2$, —$NHSO_2(Alk)_mAr$, —$N(SO_2Alk_mAr)_2$, —$NHCOAlk^2$, —$NHCONH_2$, —$NHCONHAlk^2$ or —$NHCON(Alk^2)_2$ group, where m is zero or an integer 1, $Alk^2$ is a straight or branched chain $C_{1-6}$alkylene, $C_{2-6}$alkenylene or $C_{2-6}$alkynylene chain and Ar is phenyl;

and the pharmaceutically acceptable salts, solvates hydrates and N-oxides thereof.

2. A compound according to claim 1 wherein:

$R^1$ is a 2-indanyl group; and $R^{13}$ is an —$NH_2$, —$NHAlk^2$, —$N(Alk^2)_2$, —$NHSO_2(Alk)_mAr$, —$N(SO_2Alk_mAr)_2$, —$NHCONH_2$, —$NHCONHAlk^2$ or —$NHCON(Alk^2)_2$ group.

3. A compound which is selected from the group consisting of:

(R)-4-[1-(3-(2-Indanyloxy)-4-methoxyphenyl)-2-(4-pyridyl)ethyl]aniline;

(R)-4-{2-(3-(2-Indanyloxy)-4-methoxyphenyl)-2-(4-benzylsulphonylamino)phenyl]ethyl}pyridine;

(R)-N-[4-{1-(3-(2-Indanyloxy)-4-methoxyphenyl)-2-(4-pyridyl)ethyl}phenyl]-N'-ethylurea;

and the pharmaceutically acceptable salts, solvates, hydrates and N-oxides thereof.

4. A compound according to claim 3 which is (R)-4-{2-(3-(2-Indanyloxy)-4-methoxyphenyl)-2-(4-benzylsulphonylamino)phenyl]ethyl}pyridine; and the pharmaceutically acceptable salts, solvates, hydrates or N-oxides thereof.

5. A compound according to claim 3 which is (R)-4-[1-(3-(2-Indanyloxy)-4-methoxyphenyl)-2-(4-pyridyl)ethyl]aniline; and the pharmaceutically acceptable salts, solvates, hydrates or N-oxides thereof.

6. A compound according to claim 3 which is (R)-N-[4-{1-(3-(2-Indanyloxy)-4-methoxyphenyl)-2-(4-pyridyl)ethyl}phenyl]-N'-ethylurea; and the pharmaceutically acceptable salts, solvates, hydrates or N-oxides thereof.

7. A pharmaceutical composition comprising, in combination with a pharmaceutically acceptable carrier, excipient or diluent, a pharmaceutically-effective amount of a compound according to claim 1.

8. A method of preventing or treating an inflammatory disease in a patient comprising administering to the patient, in an amount effective to elevate intracellular levels of adenosine 3',5'-cyclic monophosphate (cAMP), a selective inhibitor of a phosphodiesterase (PDE) IV isoenzyme selected from a compound according to claim 1.

* * * * *